United States Patent
Hemerick et al.

(10) Patent No.: US 7,011,675 B2
(45) Date of Patent: Mar. 14, 2006

(54) ENDOSCOPIC STENT DELIVERY SYSTEM AND METHOD

(75) Inventors: James F. Hemerick, Champlin, MN (US); Eric Schneider, Albion, RI (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 46 days.

(21) Appl. No.: 09/843,941

(22) Filed: Apr. 30, 2001

(65) Prior Publication Data

US 2002/0161425 A1   Oct. 31, 2002

(51) Int. Cl.
*A61F 2/06* (2006.01)
(52) U.S. Cl. .................................... 623/1.12
(58) Field of Classification Search .............. 623/1.12, 623/1.11, 23.7; 606/108
See application file for complete search history.

(56) References Cited

U.S. PATENT DOCUMENTS

| | | | | | |
|---|---|---|---|---|---|
| 4,665,918 | A | * | 5/1987 | Garza et al. | |
| 5,026,377 | A | * | 6/1991 | Burton et al. | 606/108 |
| 5,100,381 | A | * | 3/1992 | Burns | 604/96 |
| 5,222,971 | A | * | 6/1993 | Willard et al. | 606/158 |
| 5,306,294 | A | * | 4/1994 | Winston et al. | 623/1 |
| 5,484,444 | A | * | 1/1996 | Braunscheiler et al. | 606/108 |
| 5,695,499 | A | * | 12/1997 | Helgerson et al. | 606/108 |
| 5,700,269 | A | * | 12/1997 | Pinchuk et al. | 606/108 |
| 5,709,703 | A | * | 1/1998 | Lukic et al. | 606/198 |
| 5,810,837 | A | * | 9/1998 | Hofmann et al. | 606/108 |
| 5,817,100 | A | * | 10/1998 | Igaki | 623/1.11 |
| 5,830,179 | A | * | 11/1998 | Mikus et al. | 604/49 |
| 5,833,694 | A | * | 11/1998 | Poncet | 623/1.11 |
| 5,851,210 | A | * | 12/1998 | Torossian | 606/108 |
| 5,954,729 | A | * | 9/1999 | Bachmann et al. | 606/108 |
| 5,968,052 | A | * | 10/1999 | Sullivan et al. | 623/1.11 |
| 6,136,006 | A | * | 10/2000 | Johnson et al. | 606/108 |
| 6,413,269 | B1 | * | 7/2002 | Bui et al. | 623/1.11 |
| 6,475,244 | B1 | * | 11/2002 | Herweck et al. | 623/23.72 |
| 6,517,569 | B1 | * | 2/2003 | Mikus et al. | 623/1.11 |
| 6,666,883 | B1 | * | 12/2003 | Seguin et al. | 623/1.16 |
| 2001/0034549 | A1 | * | 10/2001 | Bartholf et al. | 623/1.12 |

* cited by examiner

*Primary Examiner*—Michael Thaler
(74) *Attorney, Agent, or Firm*—Finnegan, Henderson, Farabow, Garrett & Dunner LLP

(57) ABSTRACT

A stent delivery system is disclosed that has an outer assembly and an inner assembly that accommodates a stent. The inner assembly further has an external assembly contact area projecting from its surface that frictionally contacts an inner surface of the outer assembly. The contact area is positioned at one end of the inner assembly, proximal to the stent accommodating area. Also disclosed is a method of using the stent delivery system.

21 Claims, 6 Drawing Sheets

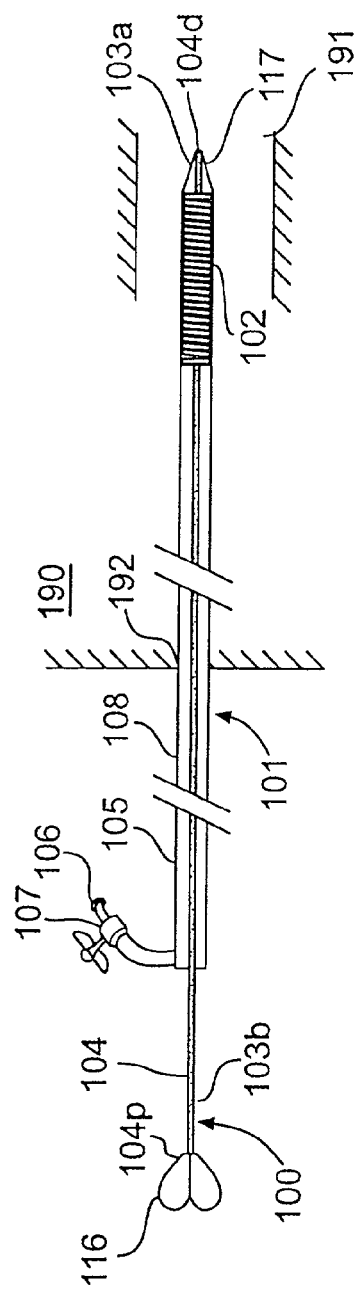
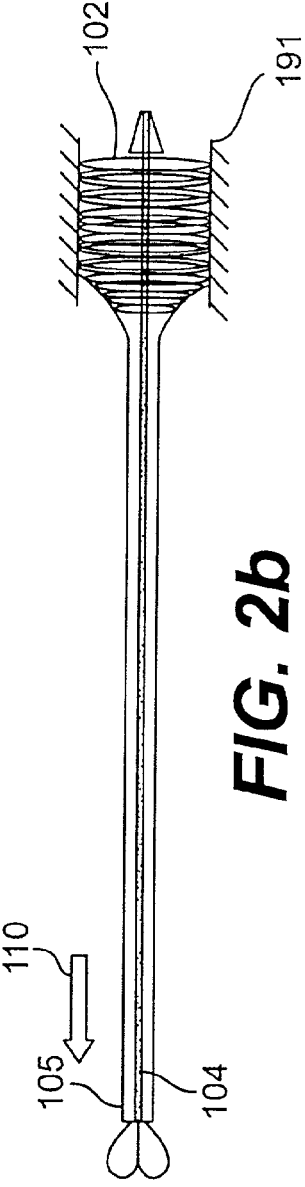
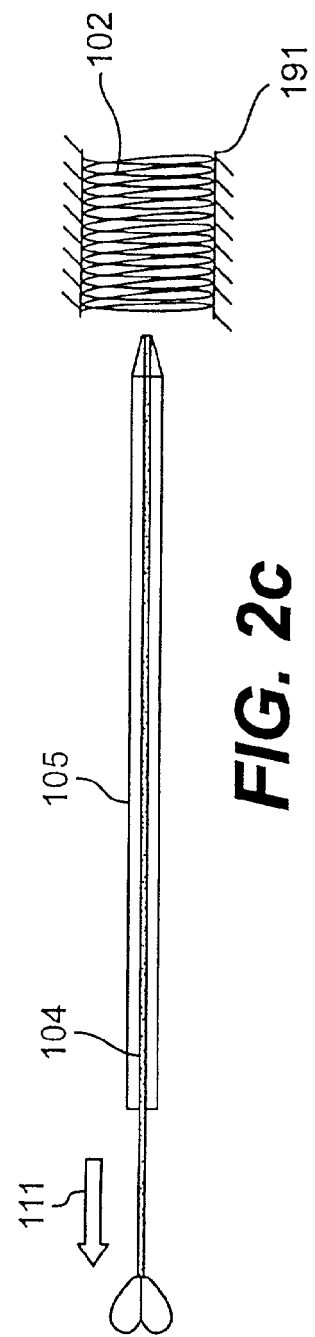
FIG. 2a
FIG. 2b
FIG. 2c

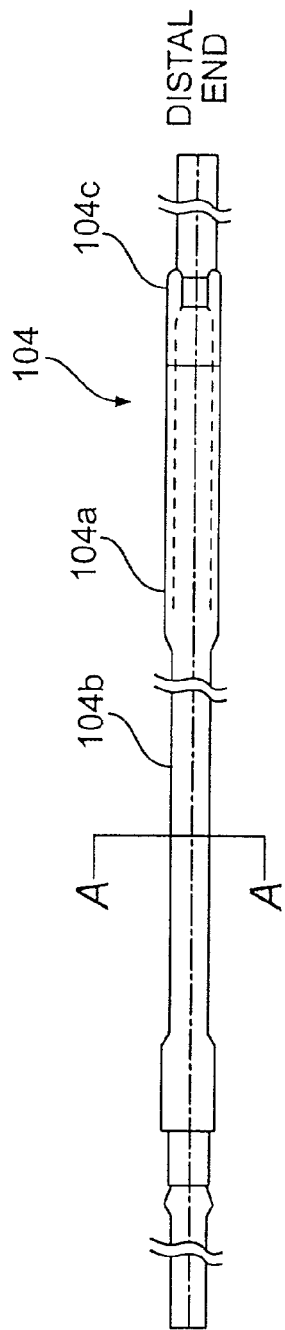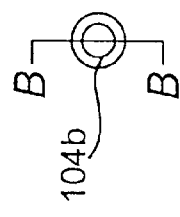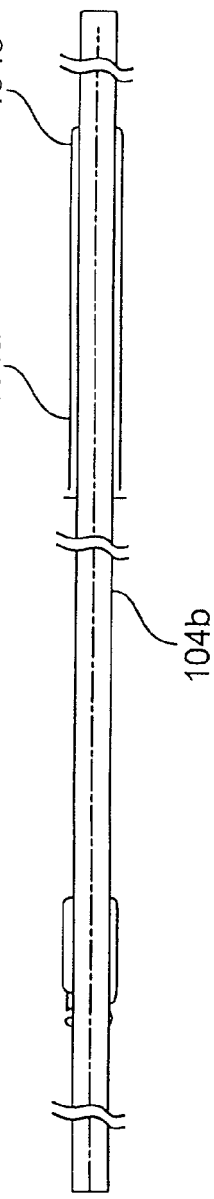

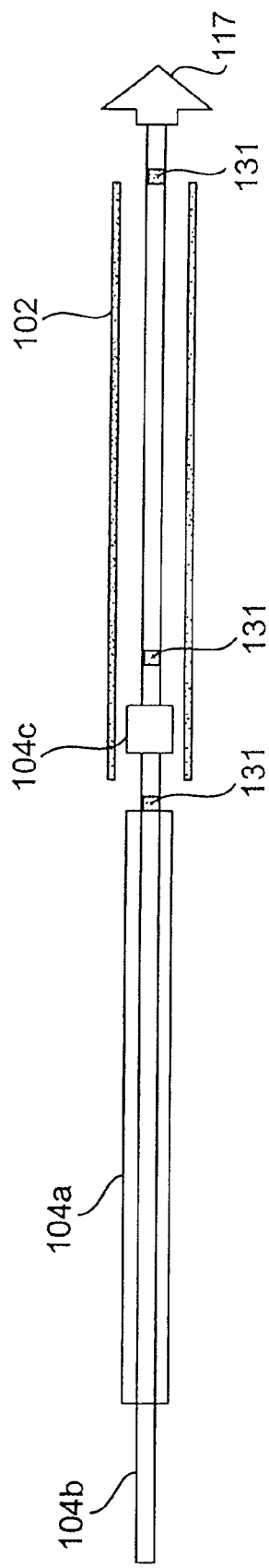
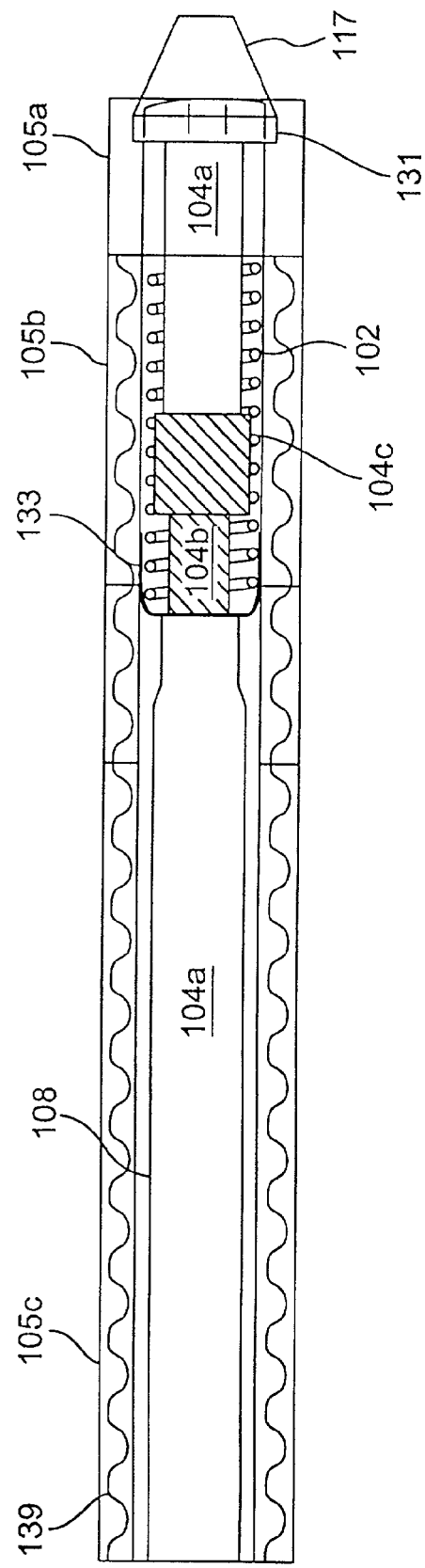
FIG. 5a
FIG. 5b

ENDOSCOPIC STENT DELIVERY SYSTEM AND METHOD

DESCRIPTION OF THE INVENTION

1. Field of the Invention

The present invention relates to stent delivery systems and methods. More particularly, the present invention relates to endoscopic stent delivery systems and methods.

2. Background of the Invention

Medical stents may be used in a variety of medical procedures. Such stents may be used to provide structural support to an anatomical structure, such as a fluid vessel, in order to prevent the structure from collapse, widen the lumens of such structures to reverse an occluded state, or allow other material to be injected or removed through the anatomical structure. Typically, such medical stents are delivered to a target anatomical structure in a tissue system via stent delivery systems. These stent delivery systems may be elongated devices that are through fluid vessels into or in proximity to target organs or tissue systems. Once in position, an outer tubular projection of the stent delivery system is retracted proximally while an inner portion, which maintains a stent in its distal end, is stationed in place. This relative movement of the outer tubular portion with respect to a stationary inner portion serves to deploy and position the stent in place. Use of such medical stents has allowed medical personnel to perform procedures that widen fluid vessels in a relatively rapid and non-invasive manner.

The deployment of a stent in tortuous anatomy, such as a blood vessel system, typically requires satisfactory force transmission with low friction interfaces. Typically, endoscopic deployment/reconstrainment forces are maintained under 10 pounds. Conventional 7.5 French endoscopic stent delivery systems may provide a low friction interface between inner and outer assemblies. However, the multi-layer exterior tube may be stiff and susceptible to kinking and stretching, resulting in damage to the delivery system during a medical procedure, thus possibly creating a hazardous condition for the patient. Other 8 French delivery systems may use a 55D Pellethane jacket on the inner assembly to fill the gap with the outer tube while maintaining flexibility. This latter design may result in excessive friction between the Pellethane jacket inner assembly and the PTFE exterior tube liner during deployment/reconstrainment in a tortuous anatomy. During deployment and reconstrainment, the forces required to create relative movement between the inner and outer assemblies accumulate with the stent resistance. The resulting cumulative force can exceed the maximum allowable force requirement for such stent delivery systems, thus possibly resulting in damage to the stent or stent delivery system during a medical procedure and, hence, contributing to a hazardous condition for the patient. Use of a relatively stiff material for the outer or inner assembly of the stent delivery device may result in kinking or breaking of the assembly, but inhibits stretching of the assembly during deployment/reconstrainment and promotes structural integrity of the assembly. For example, material with a durometer measure of 75D may be stiff enough to provide structural integrity, but may be too stiff to manipulate around corners or bends. Alternatively, use of material that is relatively soft, i.e. lower durometer material such as 55D, may result in stretching or breakage after application of a high force, but typically allows better tracking through tortuous anatomy because of the added flexibility.

Thus, it would be advantageous for a stent delivery system to have sufficient strength and stiffness to minimize kinking, stretching, and breakage, while at the same time, be flexible enough to be easily led through tortuous anatomy in the body.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

To attain the advantages and in accordance with the purpose of the invention, as embodied and broadly described herein, an exemplary embodiment of the invention includes a system for delivering a stent into an anatomical structure. The system comprises an outer tubular structure having a proximal end and a distal end and an inner elongated structure. The inner elongated structure comprises a proximal end and a distal end and is located within the outer tubular structure such that the distal end of the inner elongated structure substantially coincides with the distal end of the outer tubular structure. The inner elongated structure has a stent accommodating area on its distal end, and an external tubular structure contact area projecting from its surface and located proximal to the stent accommodating area. The external tubular structure contact area frictionally slides against an interior surface of the outer tubular structure.

In another exemplary embodiment, there is a gap between an external surface of the inner elongated structure and the interior surface of the outer tubular structure.

In another exemplary embodiment, the external tubular contact area on the inner elongated structure is constructed of Pellethane.

In yet another exemplary embodiment, there are a plurality of external tubular structure contact areas, wherein each subsequent proximal external tubular structure contact area on the surface of the inner elongated structure increases in durometer from the distal end to the proximal end of the inner elongated structure.

In another exemplary embodiment, the invention includes an inner elongated structure for a tubular stent delivery device used in deploying a stent into an anatomical structure. The inner elongated structure comprises an elongated structure, a stent accommodating area on a distal end of the elongated structure and shaped to receive a constrained length of a stent, and an engagement area projecting from the surface of the elongated structure and located proximal to the stent accommodating area. The engagement area is able to frictionally slide against an interior surface of an outer tubular structure of a stent delivery device.

In a further exemplary embodiment, the invention includes an inner elongated structure for a tubular stent delivery device used in deploying a stent into an anatomical structure. The inner elongated structure comprises an elongated structure, stent accommodating means for accommodating a constrained length of a stent at a distal end of the elongated structure, and engagement means for frictionally engaging the elongated structure with an interior surface of an outer tubular structure of a stent delivery device.

In another exemplary embodiment, the invention includes a method of deploying a stent with respect to an anatomical structure. The method includes providing a stent delivery system, wherein the system comprises an outer tubular structure having a proximal end and a distal end, an inner elongated structure having a proximal end and a distal end and is located within the outer tubular structure such that the distal end of the inner elongated structure substantially coincides with the distal end of the outer tubular structure. A stent accommodating area on the distal end of the inner elongated structure accommodates a stent. An external tubular structure contact area projecting from a surface of the inner elongated structure and located proximal to the stent accommodating area slides against an interior surface of the outer tubular structure. The method includes inserting the stent delivery system through an insertion point in a body until the distal ends of the external tubular structure and the inner elongated structure are in a position within the anatomical structure, and moving the outer tubular structure proximally while maintaining the position of the inner elongated structure, thus exposing the stent accommodating area and releasing at least part of the stent into the anatomical structure, and continuing the proximal movement of the outer tubular structure with respect to the inner elongated structure until the stent is completely deployed into the anatomical structure, and withdrawing the stent delivery system from the insertion point in the body.

In another exemplary embodiment of the method above, the stent delivery system includes a gap between an external surface of the inner elongated structure and the interior surface of the outer tubular structure.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention. In the drawings.

FIG. 2a is a longitudinal cross-section showing a stent delivery system in position within a body.

FIG. 2b is a longitudinal cross-section showing a stent delivery system during deployment of a stent into an anatomical structure within the body.

FIG. 2c is a longitudinal cross-section showing a stent delivery system being removed from the body after deployment of a stent into an anatomical structure in the body.

FIG. 4a is a side elevation of an exemplary embodiment of an inner assembly of the stent delivery system of this invention.

FIG. 4b is a planar cross-section along line A-A of the exemplary embodiment of an inner assembly of the stent delivery system of this invention depicted in FIG. 4a.

FIG. 4c is a longitudinal cross-section along line B-B of the exemplary embodiment of an inner assembly of the stent delivery system of this invention depicted in FIG. 4b.

FIG. 5a is a fragmentary cross section showing an exemplary embodiment of a portion of the inner assembly of a stent delivery system of this invention at a junction between different types of materials.

FIG. 5b is an enlarged fragmentary cross section showing an exemplary embodiment of a portion of the outer and inner assemblies of a stent delivery system of this invention at a junction between different types of materials.

FIG. 6b is a planar cross-section along line A—A of the exemplary embodiment of an inner assembly of the stent delivery system of this invention depicted in FIG. 6a.

DESCRIPTION OF THE PREFERRED EMBODIMENTS

Figure 1:
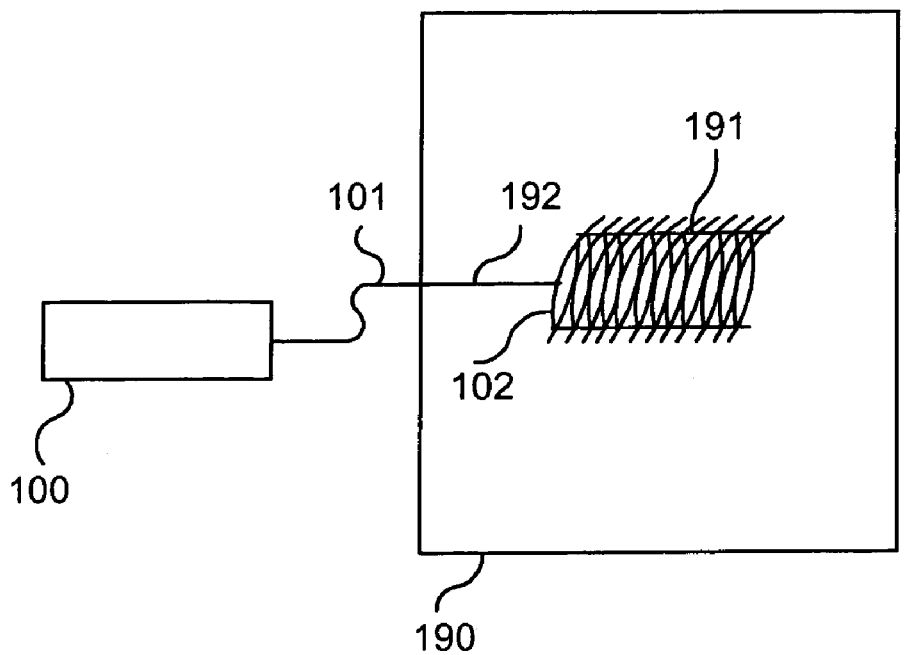
FIG. 1 is a block diagram depicting the interaction of a stent delivery system with a human body.

Reference will now be made in detail to the exemplary embodiments of the invention, examples of which are illustrated in the accompanying drawings. Wherever possible, the same reference numbers will be used throughout the drawings to refer to the same or like parts.

The present invention includes a stent delivery system and method that allows for easy stent delivery system manipulation through a human body while maintaining structural stability. Furthermore, a stent delivery system according to embodiments of this invention resists kinking and breakage by being constructed of material and in such a configuration that resists structural compromise while being led through tortuous body anatomy. The stent delivery system according to embodiments of this invention also inhibits friction by minimizing the contact area between the inner and outer assemblies, when one assembly is moving with respect to the other one of the stent delivery device, by allowing a clearance space to exist between the two assemblies. Furthermore, use of particularly resilient material on the inner assembly promotes flexibility while maintaining structural stability. In another exemplary embodiment of the invention, the inner assembly includes use of increasingly flexible material from the inner assembly's proximal to distal end, thus achieving greater flexibility of the stent delivery device where the flexibility may be needed more to wind through tortuous anatomy, closer to the distal end.

One illustrative embodiment of the invention shown in FIGS. 1–5 is a stent delivery system 100, as shown in operation in FIGS. 1 and 2a–2c. First, a method of operation of the system 100 will be described with reference to FIGS. 1 and 2a–2c to facilitate the later discussion of the structural features of the system 100.

The stent delivery system 100 may be divided into a generally tubular delivery assembly 101 and a stent 102. The delivery assembly 101 typically has multi-concentric elongated tube assemblies, which may include at least an outer tube assembly 105, that extends a substantial length of the delivery assembly 101. The delivery assembly 101 may also include an inner elongated structure 104, that may be a tubular assembly, by example, that typically extends the entire length of the delivery assembly 101, and also communicates with a stent 102 that is in contact with its distal end. The stent 102 may be a braided metallic, polymeric, or other suitable stent that typically is maintained in a stressed, compressed, and elongated state within the outer assembly 105 and is movable by the inner assembly 104. The stent 102, once placed in position into an anatomical structural 191, in a process called deployment, may act as a structural framework in maintaining the geometry of the anatomical structure 191. This interaction of the stent 102 with the outer tube and inner tube assemblies, 105 and 104, respectively, will be discussed in more detail below. Furthermore, the relative terms, proximal and distal, as used herein and throughout the specification, will be given its conventional medical definition in that proximal means relatively further away from the body and distal means relatively further into the body.

As shown in FIG. 1, the tubular delivery assembly 101 may be introduced into a patient's body 190 through an insertion point 192, which may be a natural orifice, such as the esophagus, for example, or a suitable invasive insertion point, such as through a suitable incision in the skin, as deemed by a health care worker. Most endoscopic devices are inserted through an endoscope. After introducing the delivery assembly 101 into the patient 190 through insertion point 192, the health care worker would direct the delivery assembly 101 through the natural internal anatomy of the patient until the distal end of the delivery assembly reaches a pre-determined target area, such as the anatomical structure 191. An anatomical structure 191 may include blood vessels, such as the aorta or coronary blood vessels, enzyme vessels, such as the bile duct, colonic structures and the like, or other suitable anatomical structure that may need to have a stent 102 positioned within for appropriate medical reasons.

As shown in FIG. 2a, when the stent delivery assembly 101 has been positioned into a pre-determined suitable position in the body 190, with its distal end 103a located within or in desired proximity to a target anatomical structure 191, deployment of the stent 102 may be initiated. The delivery assembly 101 typically has an inner assembly 104 and an outer assembly 105. The inner assembly 104 is usually longer than the outer assembly 105, but not necessarily. The inner assembly 104 may be an elongated structure, such as a tube with an interior that opens at both its distal end 104d and its proximal end 104p to allow for guidewire access or communication of fluids through the inner assembly 104. Such fluids that may be communicated through the inner assembly may include enzymes that may destroy structures, such as physiological stones, that block the passages of fluid vessels. Furthermore, an injection port 106, controllable by a shut-off valve 107, may allow for desired fluids to be introduced into the narrow gap space 108 between exterior surface of the interior assembly 104 and the interior surface of the outer assembly 105. Fluids that may be introduced through injection port 106 may include lubricating fluids to promote relative movement of the inner and outer assemblies with respect to each other. Additional structures that may be included on the stent delivery system 100 include a handling structure 116 to allow a health care worker to easily move the inner 104 and outer 105 assemblies with respect to each other, and a lead point 117, typically conical, that eases the directional movement of the delivery assembly 101 through body anatomy.

Deployment of the stent 102, as shown in FIG. 2b, may be initiated by holding steady the inner assembly 104 while moving the outer assembly 105 proximally in the direction of the arrow 110. This relative proximal movement of the outer assembly 105 with respect to the inner assembly 104 exposes the stent 102 housed near the distal end 103a of the outer assembly 105. The released stent 102 then may promote the structural integrity of the anatomical structure 191. Because the stent 102 may be in a compressed and elongated state within the outer assembly 105, sufficient force must be imposed on the outer assembly 105 to initiate movement with respect to the inner assembly 104. Such a force must overcome the countering frictional forces caused by the relative movement of any contacting area between the outer surface of the inner assembly 104 and the interior surface of the outer assembly 105, the radial frictional force imposed by the constrained stent on the interior surface of the outer assembly 105, and the frictional force caused by the relative movement of the outer assembly 105 with respect to the insertion point 192 and any other contacting surface.

Although health care workers typically calculate the exact release point of the stent 102 into the anatomical structure 191, any movement or shift in the position of the stent during deployment may produce undesirable positioning of the stent 102 within the anatomical structure 191. Thus, it would be desirable, before the stent 102 is fully deployed, meaning that the stent 102 has been completely released into the anatomical structure and its proximal end is no longer constrained within the outer assembly 105, to be able to reconstrain at least part of the stent 102 back into the outer assembly 105 to allow for re-positioning of the stent 102 or withdrawing the stent 102 altogether, if necessary. Hence, during deployment of the stent 102, reconstrainment may be initiated to detract the stent 102 at least partially back into the outer assembly 105. Reconstrainment is performed by a relative proximal movement of the inner assembly 104 with respect to the outer assembly 105 in the direction of the arrow 110, until the stent 102 is sufficiently retracted into the outer assembly 105 to allow re-positioning of the delivery assembly 101 in a desired position with respect to the anatomical structure 191. Reconstrainment may also be used to retract the stent 102 into the outer assembly 105 while directing the delivery assembly 101 around tight curves. After the stent 102 is fully deployed within an anatomical structure 191 and is no longer in communication with the delivery assembly 101, the delivery assembly 101 may be withdrawn from the patient in the direction shown in arrow 111, and completely removed from the patient's body 190.

FIGS. 2a–2c, as described above, have been presented to depict the relative movement of the outer and inner assemblies during deployment and possible reconstrainment. It should be noted that FIGS. 2b and 2c have been presented to show the relative movement of the two assemblies 104 and 105 and consequent stent 102 deployment, and, for sake of clarity, have not been presented with all of the details of FIG. 2a.

To promote such a relative motion of the inner assembly 104 with respect to the outer assembly 105 and to decrease the requisite force to induce such motion, it is desirable to minimize any friction between the two assemblies. Furthermore, tortuous pathways and other natural bends in a patient's internal anatomy may kink or bend the outer assembly 105, which not only may compromise the structure integrity of the stent delivery device 100, but also may increase the force required to move the inner and outer assemblies with respect to each other. Furthermore, it would be desirable for the outer assembly 105 to have improved force transmission characteristics and flexibility, particularly in the stent region, where flexibility would be most desirable.

Figure 3:
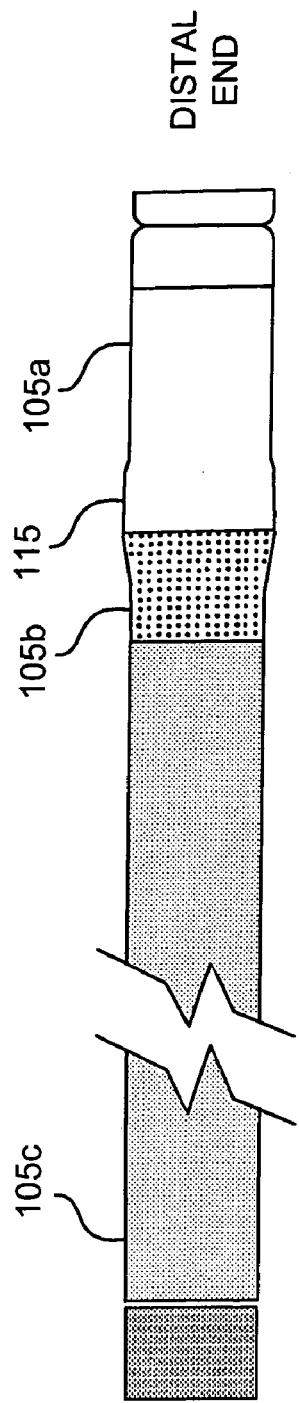
FIG. 3 is a side elevation showing an exemplary embodiment of an outer assembly of the stent delivery system of this invention.
Figure 3A:
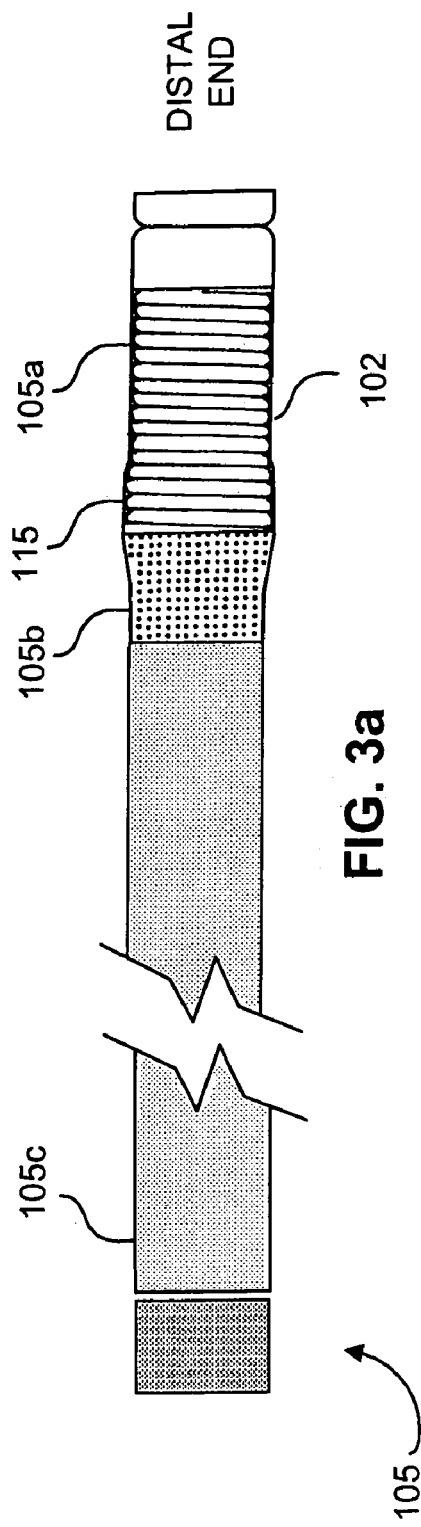
FIG. 3a is a side elevation showing a stent disposed within the outer assembly of FIG. 3.

FIGS. 3–3a and 4a–4c show the outer and inner assemblies 105 and 104, respectively, of an exemplary embodiment of an apparatus 100 of this invention. The outer assembly 105 has been described in U.S. patent application Ser. No. 09/569,445 now U.S. Pat. No. 6,726,712, which is incorporated by reference herein in its entirety. A brief review of this outer assembly 105 will be made herein for clarity. The outer assembly 105, as shown in FIG. 3, may have a non-braided clear and/or translucent distal region 105a welded at area 115 to a braided opaque proximal region 105c at a transitional region 105b for added kink resistance and improved force transmission. The distal region 105a may be 8 French, or any other dimension as long as it does not hinder movement of a stent 102 within. The clear distal region 105a partially covers the stent 102 during insertion of the delivery system 101 into a patient's body 190. As shown in FIG. 3a, region 105a may have a length that substantially coincides with a constrained length of stent 102 within the outer tubular structure. Also, the outer assembly 105 may be any material that is naturally flexible and biocompatible, such as polyether block amide (Pebax), other low density polymers, or other suitable materials. The clear and/or translucent region 105a allows a health care worker to observe the relative movement of the stent 102 during deployment such that the stent is deployed in a suitable area, and the proximal end of the stent is visible to the health care worker as the proximal end passes within the clear region 105a before stent release. The distal end of the assemblies 104, 105 and stent deployment may be viewed by any suitable known method, including, for example, an endoscope with camera system, or through fluoroscopy. The proximal region 105c extends a substantial distance along the length of the delivery system 101, and is constructed of relatively stiff material, such as 72D Pebax, to maintain the strength of the delivery system 101. The transitional region 105b is a point of adhesion between the flexible, clear and/or translucent material in the distal region 105a and the relatively stiff, strong material in the proximal region 105c.

Because the distal region 105a in the exterior tube assembly 105 may not be braid reinforced and typically is thin walled, typically 0.006"–0.008" width walls, for flexibility, it may be likely to kink around a bend unless internally supported. Thus, the inner assembly 104 may include an inner elongated structure 104b, which may be constructed of polyetheretherketone (PEEK), having one or more jackets 104a, which may be made of Pellethane, along its length to minimize friction when the one or more jackets 104a contact the interior surface of the outer assembly 105. Furthermore, a jacket 104a may provide interior support to the distal exterior tube region 105a. As shown in FIGS. 4a–4c, the layer of Pellethane typically is on a shortened jacket 104a of a conventional material, such as PEEK, used as a material for the inner elongated structure 104b, which will be described as a tube in the illustrated embodiments. This jacket 104a is of sufficient length to support the non-braided, clear and/or translucent portion of the exterior tube 105a during, for example, reconstrainment around a curve. The jacket 104a typically is longer than the longest constrained length of the stent 102 to provide support for the stent 102. The combination of the inner assembly 104, having a jacket 104a with a layer of pellethane thereon, with the outer assembly 105, results in an endoscopic delivery system with excellent force transmission, a flexible stent region, and low requisite deployment/reconstrainment forces in tortuous anatomies.

To further inhibit friction and promote ease in operation of the stent delivery system 100, a gap 108 may be created between the outer surface of the inner assembly 104 and the inner surface of the outer assembly 105. This gap 108 may be approximately 0.005", but may range from 0.004 to 0.008". The gap 108 may be increased as the diameter of the tubes creating its walls are increased. Furthermore, there may be a short length in neckdown to fit into the stainless steel counterbore to support the proximal region. Such support of the proximal region is similar to a flexible transition.

The distal jacket 104a may be thermally attached proximal to the distal portion of the interior tube 104b. This jacket 104a may be a length that would support a constrained length of the stent 102, which typically is longer than its unconstrained length. A typical length for the jacket 104a may be approximately 130 mm. However, the length of the jacket 104a may be changed to accommodate stents 102 of different lengths. More particularly, the length of the jacket 104a may be that of the longest constrained stent length in order to provide internal support to the exterior tube assembly 105 until the point where the stent 102 is fully deployed into the anatomical structure 191. The proximal end of the stent 102 may be in communication with a holding cup 133 that holds the proximal end of the stent 102 and a holding sleeve 104c that is attached near the distal end of the inner assembly 104. The holding sleeve 104c may be an opaque sheet of plastic, such as Tecothane, for example, in a distinct color, such as red, for example, that holds the proximal end of the stent 102 and also serves as a visual indicator to a health care worker of the proximal end of the stent 102. The holding sleeve 104c may accommodate the stent 102 by friction, such as by laser cutting polymer from wire to create bare stent ends, and leaving silicone ribs on the backside of the wire, thus providing a high friction surface that comes in contact with the holding sleeve 104c. Additionally, during deployment, visual signal bands 131 that may be adjacent the holding sleeve 104c, and which may be radiopaque such as, for example, tantalum or platinum, may become visible through a fluoroscope through the clear and/or translucent portion of the exterior tube 105a, such that a health care worker would be signaled that the stent 102 is close to being deployed, thus if reconstrainment is necessary to re-position the stent 102, it would be time to do so. The stent 102 is free to move independently of the outer assembly 105 as directed by the inner assembly 104. As discussed above, to activate deployment of the stent 102, the outer assembly 105 typically is retracted proximally which moves the non-braided region 105a over the inner member jacket 104a. During reconstrainment of the stent 102, the inner assembly 104 may be pulled proximally while the exterior assembly 105 remains stationary. The low friction response of the jacket 104a with the interior lining of the outer assembly 105 typically results in less resistance than conventional stent deployment assemblies because there is a limited area of contact between the two assemblies. In an exemplary embodiment, Pellethane tubing is used as the jacket 104a material and PTFE is used as the interior surface lining of the exterior assembly 105. Alternatively or additionally, the surface of the jacket 104a may be lubricated with a suitable lubricant such as MDX silicone to further decrease frictional forces opposing relative movement between the two assemblies. Other materials, besides Pellethane, also may be used for the jacket 104a as long as the materials exhibit relatively low frictional forces when in contact with the interior surface of the outer assembly 105. Such alternative materials for the jacket 104a may include low-density polyethylene.

FIGS. 5a and 5b show exemplary embodiments of the relationship between different components of a stent delivery device 101, including the stent 102, outer assembly 105, and inner assembly 104. As shown in these figures, an outer assembly 105, including a clear and/or translucent outer portion 105a, a transition region 105b, and a opaque braided region 105c, surrounds an inner assembly 104, including multiple Pellethane jackets 104a along an interior tube 104b. A holding sleeve 104c assists in holding and identifying the proximal end of a stent 102. At the distal end of the stent 102 is a marker band 131 that marks the front edge of the stent 102, thereby assisting in proper stent position during deployment. The marker band 131 may be radiopaque to be visible under fluroscopy. The lead point 117 is positioned distal to the marker band 131. The braid 139 in the outer assembly 105 may extend across the opaque region 105c and the transition region 105b, thereby partially covering the stent 102 held within the outer assembly 105. Part of the stent 102, however, may be visible through the clear and/or translucent region 105a. As stated above, during stent 102 deployment, when the marker band 131 adjacent the holding sleeve 104c is visible through the clear region 105a under fluoroscopy, a health care worker is signaled that the stent 102 is nearly completely deployed and, thus, any reconstrainment to re-position the stent 102 within the anatomical structure 191, if needed, should be initiated. Otherwise, the stent 102 will be completely deployed into the anatomical structure 191 and released from the delivery system 101.

Figure 6A:
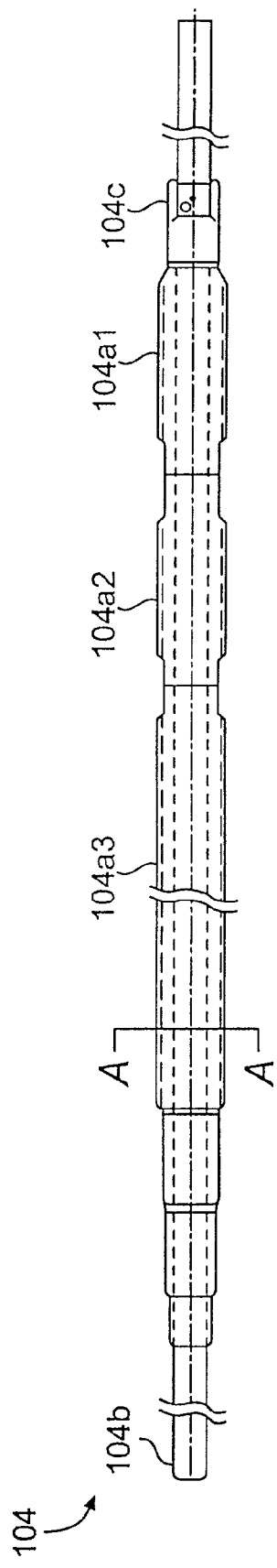
FIG. 6a is a side elevation of another exemplary embodiment of an inner assembly of the stent delivery system of this invention.
Figure 6B:
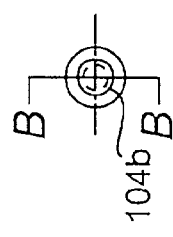
Figure 6C:
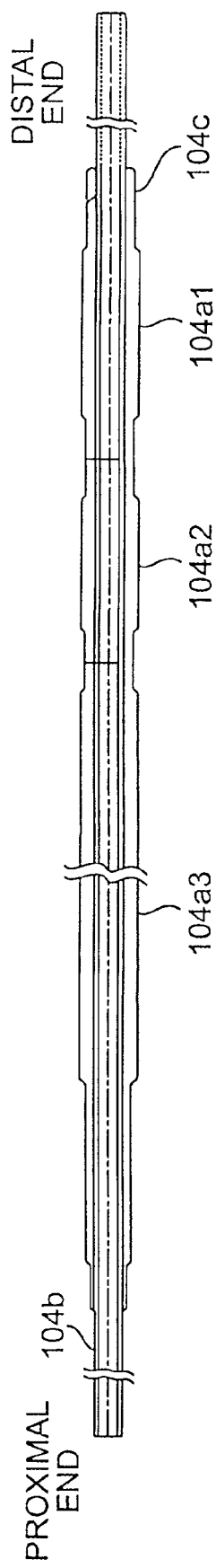
FIG. 6c is a longitudinal cross-section along line B—B of the exemplary embodiment of an inner assembly of the stent delivery system of this invention depicted in FIG. 6b.

Another exemplary embodiment of the inner assembly 104 is shown in FIGS. 6a–6c. In this embodiment, multiple contact areas, such as the three exemplary areas shown as 104a1–104a3, project on the surface of inner tube 104b. These multiple contact areas 104a1–104a3 function much like the jacket 104a in FIG. 4 in communicating with the interior surface of an outer assembly 105. The inner assembly 104 in FIGS. 6a–6c exhibits more controlled resiliency and strength by having multiple contact areas 104a1–104a3 that decrease in stiffness, as measured by durometer value, as the contact areas are more distally located. Stated differently, a durometer measure of contact area 104a1 may be less than a durometer measure of contact area 104a2, which may itself be less than a durometer measure of contact area 104a3. Exemplary embodiments of contact area durometer measure may be 55D for contact area 104a1, 65D for contact area 104a2, and 75D for contact area 104a3. This use of sequentially increasing durometer material on an inner assembly 104 from a distal end proximally promotes flexibility in the delivery system 101 where it would benefit greatly, near the distal end. The lower durometer material is more flexible than higher durometer material. Thus, the delivery system 101 will gain in flexibility towards its distal end, where the stent delivery device may require a greater degree of precision in winding through tortuous anatomy. However, the structural integrity of the overall stent delivery device 100 will be maintained because a higher durometer material is used throughout a significant length of the inner assembly 104.

Other embodiments of the invention will be apparent to those skilled in the art from consideration of the specification and practice of the invention disclosed herein. For example, the sequential increase in the durometer measure of subsequent contact areas of FIGS. 6a–6c may occur at every other contact area, or other such trend, as long as there is an increase in flexibility from a proximal region to a distal region of the inner assembly 104. Also, there may be more than one distinct jacket layer 104a of Pellethane used in the illustrated embodiment depicted in FIGS. 4a–4c, or stated differently, each of the jacket layers 104a1, 104a2, and 104a3 in FIGS. 6a–6c may be Pellethane. More than or less than three jacket layers are possible in the illustrated embodiment depicted in FIGS. 6a–6c. Furthermore, the length of the clear and/or translucent region 105a may be changed to suit the preference of health care workers so that either more or less of the constrained length of the stent 102 may be visible during deployment/reconstrainment. It is intended that the specification and examples be considered as exemplary only, with a true scope and spirit of the invention being indicated by the following claims.

What is claimed is:

1. A system for delivering a stent into an anatomical structure, the system comprising:
   an outer tubular structure having a proximal end, a distal end, an inner surface defining a lumen, and an outer surface, wherein the outer tubular structure has a translucent region at the distal end and the translucent region has a length less than a constrained length of a stent placed within the outer tubular structure, wherein the outer tubular structure is devoid of braiding along the length of the translucent region between the inner and outer surfaces;
   an inner elongated structure having a proximal end and a distal end, the inner elongated structure being located within the outer tubular structure such that the distal end of the inner elongated structure substantially coincides with the distal end of the outer tubular structure;
   a stent accommodating area on the distal end of the inner elongated structure, the stent accommodating area accommodating the stent; and
   an external tubular structure contact area projecting from a surface of the inner elongated structure and located closer to a proximal end of the stent accommodating area than a distal end of the stent accommodating area, the external tubular structure contact area frictionally sliding against an interior surface of the outer tubular structure,
   wherein the translucent region is coextensive with at least a portion of the stent accommodating area.

2. The system of claim 1, further comprising:
   a gap between an external surface of the inner elongated structure and the interior surface of the outer tubular member.

3. The system of claim 1, further comprising:
   at least one marker band on the inner elongated structure proximate the stent accommodating area.

4. The system of claim 1, wherein the external tubular structure contact area on the inner elongated structure is constructed of Pellethane.

5. The system of claim 1, wherein the external tubular structure contact area on the inner elongated structure comprises a plurality of external tubular structure contact areas projecting from the surface of the inner elongated structure.

6. The system of claim 5, wherein each external tubular structure contact area on the inner elongated structure is separated from other external tubular structure contact areas.

7. The system of claim 6, wherein each subsequently proximal external tubular structure contact area on the surface of the inner elongated structure increases in durometer from the distal end to the proximal end of the inner tubular structure.

8. The system of claim 7, wherein the most distal external tubular structure contact area on the surface of the inner elongated structure has a durometer measure of approximately 55D.

9. The system of claim 8, wherein there are three external tubular structure contact areas.

10. The system of claim 9, wherein the durometer measures of the three external tubular structure contact areas on the surface of the inner tubular structure from the distal end proximally are approximately 55D, approximately 65D, and approximately 75D.

11. A method of deploying a stent with respect to an anatomical structure, the method comprising:
providing a stent delivery system, the system comprising:
an outer tubular structure having a proximal end, a distal end, an inner surface defining a lumen, and an outer surface, wherein the outer tubular structure has a translucent region at the distal end and the translucent region has a length less than a constrained length of a stent within the outer tubular structure, wherein the outer tubular structure is devoid of braiding along the length of the translucent region between the inner and outer surfaces;
an inner elongated structure having a proximal end and a distal end, the inner elongated structure being located within the outer tubular structure such that the distal end of the inner elongated structure substantially coincides with the distal end of the outer tubular structure;
a stent accommodating area on the distal end of the inner elongated structure accommodating the stent; and
an external tubular structure contact area projecting from a surface of the inner elongated structure and located closer to a proximal end of the stent accommodating area than a distal end of the stent accommodating area, the external tubular structure contact area able to frictionally slide against an interior surface of the outer tubular structure,
wherein the translucent region is coextensive with at least a portion of the stent accommodating area;
inserting the stent delivery system through an insertion point in a body until the distal ends of the external tubular structure and the inner elongated structure are in a position within the anatomical structure;
moving the outer tubular structure proximally while maintaining the position of the inner elongated structure, thus exposing the stent accommodating area and releasing at least part of the stent into the anatomical structure;
continuing the proximal movement of the outer tubular structure with respect to the inner elongated structure until the stent is completely deployed into the anatomical structure; and
withdrawing the stent delivery system from the insertion point in the body.

12. The method of claim 11, wherein the stent delivery system further comprises:
a gap between an external surface of the inner elongated structure and the interior surface of the outer tubular member.

13. The method of claim 11, wherein the stent delivery system further comprises:
at least one marker band on the inner elongated structure proximate the stent accommodating area.

14. The method of claim 11, further comprising:
before completely deploying the stent into the anatomical structure, moving the inner elongated structure proximally while maintaining the position of the outer tubular structure, thus retracting at least part of the stent from the anatomical structure back into the stent accommodating area; and
re-positioning the stent delivery system to a new position with respect to the anatomical structure.

15. The method of claim 11, wherein the external tubular structure contact area on the inner elongated structure is constructed of Pellethane.

16. The method of claim 11, wherein the external tubular structure contact area on the inner elongated structure comprises a plurality of external tubular structure contact areas projecting from the surface of the inner elongated structure.

17. The method of claim 16, wherein each external tubular structure contact area on the inner elongated structure is separated from other external tubular structure contact areas.

18. The method of claim 17, wherein each subsequently proximal external tubular structure contact area on the surface of the inner elongated structure increases in durometer from the distal end to the proximal end of the inner tubular structure.

19. The method of claim 18, wherein the most distal external tubular structure contact area on the surface of the inner elongated structure has a durometer measure of approximately 55D.

20. The method of claim 19, wherein there are three external tubular structure contact areas.

21. The method of claim 20, wherein the durometer measures of the three external tubular structure contact areas on the surface of the inner tubular structure from the distal end proximally are approximately 55D, approximately 65D, and approximately 75D.

* * * * *